(12) United States Patent
Duindam et al.

(10) Patent No.: US 9,636,040 B2
(45) Date of Patent: May 2, 2017

(54) STEERABLE FLEXIBLE NEEDLE WITH EMBEDDED SHAPE SENSING

(71) Applicant: Intuitive Surgical Operations, Inc., Sunnyvale, CA (US)

(72) Inventors: Vincent Duindam, Mountain View, CA (US); Giuseppe Maria Prisco, Pontedera (IT); David Q. Larkin, Menlo Park, CA (US); Simon P. DiMaio, San Carlos, CA (US); Dorin Panescu, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 453 days.

(21) Appl. No.: 13/751,462

(22) Filed: Jan. 28, 2013

(65) Prior Publication Data

US 2013/0204124 A1    Aug. 8, 2013

Related U.S. Application Data

(60) Provisional application No. 61/599,015, filed on Feb. 15, 2012, provisional application No. 61/594,959, filed on Feb. 3, 2012.

(51) Int. Cl.
*A61B 5/06* (2006.01)
*A61B 17/3209* (2006.01)
(Continued)

(52) U.S. Cl.
CPC .......... *A61B 5/065* (2013.01); *A61B 10/0233* (2013.01); *A61B 17/3209* (2013.01); *A61B 17/3468* (2013.01); *A61B 17/3403* (2013.01); *A61B 2010/045* (2013.01); *A61B 2017/003* (2013.01); *A61B 2017/00331* (2013.01);
(Continued)

(58) Field of Classification Search
CPC ............ A61B 17/3468; A61B 17/3209; A61B 17/3403; A61B 2017/3409; A61B 2019/5261
See application file for complete search history.

(56) References Cited

U.S. PATENT DOCUMENTS 6,203,493 B1 * 3/2001 Ben-Haim .................... 600/117
6,389,187 B1   5/2002 Greenaway et al.
(Continued)

FOREIGN PATENT DOCUMENTS

WO    WO-2008131303 A2    10/2008

OTHER PUBLICATIONS

Alpium, P. et al., "Ultra-Sensitive Shape Sensor Test Structures Based on Piezo-Resistive Doped Nanocrystalline Silicon," NanoSpain2008 Conference, Apr. 14-18, 2008, Braga, Portugal, 2 pages.
(Continued)

*Primary Examiner* — Laura Bouchelle

(57) ABSTRACT

A surgical system includes a flexible steerable needle and a shape sensor for measuring the shape of the needle. The surgical system can be manual (e.g., laparoscopic), robotic, or any combination of the two. By directly measuring the shape of the needle, complex and potentially inaccurate modeling of the needle to determine trajectory and insertion depth can be avoided in favor of much more robust direct measurement and modeling of needle shape and/or pose.

37 Claims, 10 Drawing Sheets

(51) Int. Cl.
- *A61B 10/02* (2006.01)
- *A61B 17/34* (2006.01)
- *A61B 17/00* (2006.01)
- *A61B 10/04* (2006.01)
- *A61B 34/10* (2016.01)
- *A61B 34/20* (2016.01)

(52) U.S. Cl.
CPC ............... *A61B 2017/00991* (2013.01); *A61B 2034/107* (2016.02); *A61B 2034/2051* (2016.02); *A61B 2034/2061* (2016.02)

(56) References Cited

U.S. PATENT DOCUMENTS

| | | | |
|---|---|---|---|
| 6,470,205 B2 * | 10/2002 | Bosselmann et al. | 600/424 |
| 6,508,802 B1 * | 1/2003 | Rosengart | A61M 25/0084 |
| | | | 604/164.01 |
| 7,670,350 B2 * | 3/2010 | Selis | A61B 19/54 |
| | | | 600/431 |
| 7,720,322 B2 | 5/2010 | Prisco | |
| 7,772,541 B2 | 8/2010 | Froggatt et al. | |
| 7,781,724 B2 | 8/2010 | Childers et al. | |
| 7,824,328 B2 | 11/2010 | Gattani et al. | |
| 8,050,523 B2 | 11/2011 | Younge et al. | |
| 8,488,130 B2 | 7/2013 | Duindam et al. | |
| 8,649,847 B1 * | 2/2014 | Park | A61M 25/0158 |
| | | | 600/433 |
| 2002/0087101 A1 | 7/2002 | Barrick et al. | |
| 2005/0149097 A1 * | 7/2005 | Regnell | A61M 25/0068 |
| | | | 606/191 |
| 2005/0228274 A1 | 10/2005 | Boese et al. | |
| 2006/0013523 A1 | 1/2006 | Childlers et al. | |
| 2006/0184016 A1 | 8/2006 | Glossop | |
| 2007/0093703 A1 | 4/2007 | Sievert et al. | |
| 2007/0293721 A1 | 12/2007 | Gilboa | |
| 2010/0249507 A1 | 9/2010 | Prisco et al. | |
| 2011/0319815 A1 | 12/2011 | Roelle et al. | |
| 2011/0319910 A1 * | 12/2011 | Roelle et al. | 606/130 |
| 2012/0143029 A1 | 6/2012 | Silverstein et al. | |
| 2012/0289777 A1 | 11/2012 | Chopra et al. | |

OTHER PUBLICATIONS

Dunlop R., et al., "A Nitinol Wire Actuated Stewart Platform," Proceedings of the Australasian Conference on Robotics and Automation, 2002, pp. 122-127.

Herrera-May A.L., et al., "Electromechanical Analysis of a Piezoresistive Pressure Microsensor for Low-pressure Biomedical Applications," Revista Mexicana De Fisica, 2009, vol. 55 (1), pp. 14-24.

International Search Report and Written Opinion for Application No. PCT/US2013/023398, mailed on Jun. 13, 2013, 17 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Extended European Search Report for Application No. EP20130743290, mailed on Jun. 24, 2015, 6 pages.

\* cited by examiner

STEERABLE FLEXIBLE NEEDLE WITH EMBEDDED SHAPE SENSING

CROSS REFERENCE TO RELATED APPLICATIONS

This application claims the benefit of U.S. Provisional Application No. 61/599,015 filed Feb. 15, 2012 and U.S. Provisional Application No. 61/594,959 filed Feb. 3, 2012, which are incorporated by reference herein in their entirety.

BACKGROUND

Aspects of this disclosure are related to shape sensing in a minimally invasive surgical instrument, and more particularly to the incorporation of shape sensing capabilities into a flexible needle.

Minimally invasive surgical procedures typically rely on some sort of instrument position monitoring to ensure proper access to, and behavior at, the target surgical location. Conventional minimally invasive surgical instruments are generally either formed from generally rigid, elongate elements (e.g., laparoscopic or robotic systems) or highly flexible systems designed to follow a predetermined anatomic path (e.g., angioplasty balloon catheters). In either case, position monitoring typically involves localized tracking.

For example, the overall shape of an instrument formed from rigid bodies can be determined via monitoring of just the extrema (e.g., the joints and ends) of those elements. For example, the shape of a rigid three-linkage robotic arm having two rotational joints (single degree of freedom for each joint) can be modeled using measurements from just the two rotational joints.

For catheter-based procedures, it is generally the catheter tip position that is critical, with the length of the catheter simply residing within a vessel in the body. For example, in an angioplasty procedure, the guidewire and/or balloon catheter tip must be positioned at the arterial blockage, and so the guidewire/balloon catheter tip is monitored (typically via direct visualization). The remaining guidewire/catheter length is not actively monitored, except in an incidental sense to the extent the remaining length is shown during fluoroscopic visualization of the tip advancement.

However, increasingly more complex minimally invasive surgical systems can require enhanced instrument position monitoring for safe and effective use. For example, the development of flexible, steerable needles provides an opportunity for procedures such as biopsy and/or therapeutic treatment, such as ablation treatments or radioactive seeds placement, at internal locations that would be problematic to access via a straight path—e.g., if it would be undesirable to puncture any intervening anatomy. Flexible, steerable needles can be delivered to the target site by direct penetration into the tissue, such as for example in the case of transcutaneous biopsy needles for the liver or other internal organs. Flexible, steerable needles can be delivered to the target site making use of the channel of an endoscope or a catheter, such as for example in the case of transluminal lung or stomach biopsy.

As used herein, steerable needles refer to a broad category of flexible needles with control inputs at the base (i.e., outside the body of the patient) and distal regions meant for piercing or puncturing target tissue. Depending on the shape and mechanical properties of the needle, interaction forces between the needle and the patient anatomy (i.e., the target tissue and/or any intervening anatomy between the surgical entry point and the target tissue) can cause the needle to deflect, such that steering can be provided by simply applying rotation to the base of the needle. Alternatively or additionally, a steerable needle can include active actuators to provide shaping and directionality. Steerable needles generally have a high axial stiffness and a tip shape that allows them to puncture or penetrate tissue with minimal axial compression, as compared to catheter-type devices that have a low axial stiffness and are not suited to penetrate or puncture.

Note that the term "flexible" in association with a steerable needle should be broadly construed. In essence, it means the needle can be bent without harm. For example, a flexible steerable needle may include a series of closely spaced components that are similar to "vertebrae" in a snake-like arrangement. In such an arrangement, each component is a short link in a kinematic chain, and movable mechanical constraints (e.g., pin hinge, cup and ball, and the like) between each link may allow one (e.g., pitch) or two (e.g., pitch and yaw) degrees of freedom (DOF) of relative movement between the links. As another example, a flexible steerable needle may be continuous, such as a closed bendable tube (e.g., nitinol, polymer, and the like) or other bendable piece (e.g., kerf-cut tube, helical coil, and the like).

At the same time, the use of a flexible needle in a minimally invasive fashion can be significantly more complicated than conventional robotic or laparoscopic procedures. Not only is the variability in the actual shape of a steerable needle much greater than that of a linkage of rigid elements, but the needle flexibility can greatly increase susceptibility to deviation from a target trajectory due to variations in tissue characteristics (e.g., scar tissue, or otherwise denser than expected tissue, may result in greater than expected curvature of the flexible needle).

Accordingly, it is desirable to provide a steerable needle system that can be effectively used in minimally invasive surgical procedures.

SUMMARY

By incorporating a shape sensor into a flexible needle, the shape and/or surgical trajectory of such a needle can be effectively monitored and controlled to enable efficient and effective procedure performance.

As used herein, steerable needles refer to a broad category of flexible needles with control inputs at the base (i.e., outside the body of the patient) and distal regions meant for piercing or puncturing target tissue. The control inputs allow the needle to be guided along a desired surgical trajectory to a target location within the patient. In some embodiments, the needle may include a tip geometry that imparts a directional motion as the tip passes through tissue, such that the control inputs can simply be a handle(s) or other control to axially rotate the needle. In other embodiments, the needle may include wires, cables, or any other actuation mechanism to allow for more direct control over the shape and direction of travel of the needle. In such embodiments, the control inputs would be configured to provide the appropriate manipulation or actuation energy to the actuation mechanism(s) of the needle.

Depending on the shape and mechanical properties of the needle, interaction forces between the needle and the patient anatomy (i.e., the target tissue and/or any intervening anatomy between the surgical entry point and the target tissue) can cause the needle to deflect and move along curved trajectories. The shape and/or direction of these trajectories can be influenced through the control inputs.

Steerable needles can be used in minimally invasive clinical procedures for diagnosis and treatment of difficult to reach targets, e.g., in prostate biopsy and brachytherapy.

In some embodiments, a steerable needle can be a highly flexible (e.g., nitinol) needle with an asymmetric beveled tip and control inputs for insertion and shaft rotation. As it is inserted into tissue, the needle moves approximately along a circular path in the direction of the bevel. Rotating the needle shaft causes the bevel direction to change, thereby causing the needle shape and/or trajectory direction to change as the needle is moved through the patient anatomy. In other embodiments, a steerable needle can be a highly flexible (e.g., nitinol) needle with a pre-bent tip section and control inputs for insertion and shaft rotation. In this case, the needle moves along an approximately circular trajectory in the direction of the pre-bent tip (the lowest-energy state of the needle), wherein shape and/or trajectory direction changes can be effected via needle shaft rotation. In yet other embodiments, a steerable needle can be a highly flexible needle with an asymmetric tip (either beveled or pre-bent) that is controlled from the base by shaft insertion, shaft rotation, and bending at the entry point to control shape and/or trajectory direction. In various other embodiments, a steerable needle can be a concentric-tube device in which several flexible pre-bent tubes are assembled concentrically. The external control inputs determine the relative orientation and sliding amount of the different flexible tubes. The tip position and orientation can be changed by sliding and rotating the pre-bent tubes using the control inputs, thereby enabling control over shape and/or trajectory direction in use.

In some embodiments, a steerable needle can be fitted with a shape sensor(s) that measures the continuous shape of the needle. The sensor can be placed in a separate lumen in the wall of the needle, tacked in place (optionally in grooves) on the inside or outside of the needle wall, be removably inserted into the lumen of the needle (e.g., as part of a stylet), or otherwise coupled to the flexible needle along at least a portion of its length. The use of the interior lumen of the needle beneficially avoids the requirement of extra wall thickness or size.

The information obtained from the shape sensor can be used in various ways. For example, from the measured shape the total insertion depth into the tissue as well as the tip position and orientation can be determined. These variables can be used in a servo-loop to precisely control the needle insertion and orientation—instead of measuring just the proximal insertion and rotation amounts on the control inputs and assuming perfect transfer to the tip, the shape sensor can be used to directly measure the distal insertion and rotation, independent from the torsional and axial flexibility of the needle and the effects of friction and normal forces between the needle and the tissue.

In another embodiment, the measured tip position and orientation (as computed from the shape information) can be used in planning algorithms that compute feasible paths from the current needle position to the target location. The shape sensor can be used to measure the needle pose in place of or in addition to (potentially imprecise and noise) imaging techniques.

In another embodiment, the shape sensor can be used to identify unknown model parameters in the biomechanical model of the tissue, as used in the planning software. For example, the bend radius of the trajectory of a steerable needle depends on the properties of the needle as well as the local properties of the surrounding tissue. These properties are hard to predict, but the shape sensor can be used to measure current actual bend radius of the trajectory to update model parameters.

In another embodiment, where one of the control inputs is bending the needle base near the entry point of the tissue, the shape sensor information, in conjunction with the needle material properties, can be used to estimate and locally update the kinematic mapping between needle base motions and needle tip motions. This mapping can be used to control the base of the needle for desired tip motion.

In another embodiment, the shape measurements can be used to detect undesired motions of the needle shaft, such as buckling and large deviations from the expected or allowed path. In conjunction with a mechanical model of the needle, the measured needle shape can also be used to estimate forces applied along the needle shaft. This could be used to identify points where high force is being applied to tissue.

In another embodiment, the shape sensor can be used in conjunction with imaging techniques to improve registration of the needle relative to preoperative data. The base, or some other portion of the shape sensor, can be registered to the image coordinate space by attaching an image-able fiducial to a portion of the fiber, or docking a fixed reference point on the fiber to a visible fiducial feature on the patient, or similar. The intraoperative imaging would provide a means to adapt needle trajectory in response to tissue motion or deformation. The measured shape of the needle could be used to assist in detecting and localizing the needle in intraoperative images, such that its position/orientation with respect to anatomical targets could be measured.

In another embodiment, the shape sensor can be used, in conjunction with a driving mechanism, to provide input in order to manually or automatically control an actuator that steers the flexible needle during a medical procedure.

DETAILED DESCRIPTION

Figure 1A:
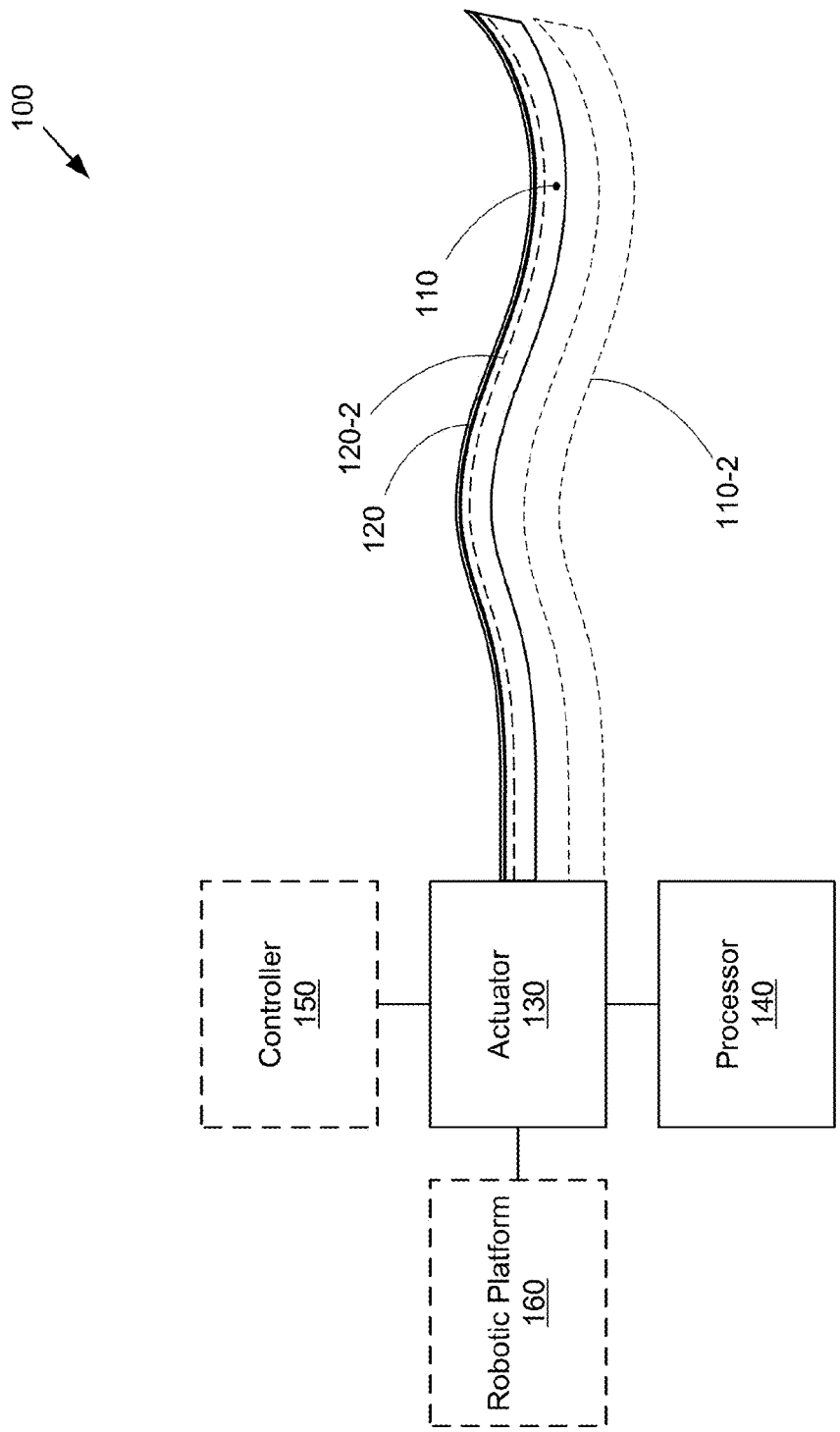
FIG. 1A is a block diagram of a minimally invasive surgical system that includes a steerable needle incorporating shape sensing.

By incorporating a shape sensor into a flexible needle, the shape and/or surgical trajectory of such a needle can be effectively monitored and controlled to enable efficient and effective procedure performance.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

FIG. 1 shows an exemplary minimally invasive surgical system 100 that includes a steerable needle 110 that can be manipulated during a surgical procedure by an actuator 130. As used herein, steerable needles refer to a broad category of flexible needles with control inputs (i.e., actuator 130) at the base (i.e., outside the body of the patient) and distal regions meant for piercing or puncturing target tissue. Such needles can be used for diagnosis and/or treatment of difficult to access targets in a patient, such as in prostate biopsy, lung biopsy, liver biopsy, and brachytherapy, among others. Note that in various embodiments, system 100 can include any number of steerable needles, as indicated by optional steerable needle 110-2 (along with any actuation, control, sensing, and/or processing elements required for the additional needles 110).

Actuator 130 can manipulate needle 110, for example, by steering needle 110 along a desired surgical trajectory to a target location within the patient, changing the shape of needle 110, and/or changing the orientation of needle 110. As described in greater detail below, in some embodiments, the needle may include a tip geometry that imparts a directional motion as the tip passes through tissue, such that the control inputs can simply be a handle(s) or other control to axially rotate the needle. In other embodiments, the needle may include wires, cables, or any other actuation mechanism to allow for more direct control over the shape and direction of travel of the needle. In such embodiments, the control inputs would be configured to provide the appropriate manipulation or actuation signals/energy to the actuation mechanism(s) of the needle.

System 100 further includes a continuous shape sensor 120 that is substantially aligned with at least a portion of steerable needle 110. Regardless of the specific steering mechanism provided for needle 110, usability of system 100 in a minimally invasive surgical procedure is enhanced by the inclusion of shape sensor 120. As described in greater detail below, the data read by shape sensor 120 is acquired and converted into usable shape information by a processor 140. The shape information can then be used to guide further manipulation of needle 110. A shape sensor is an elongate sensor that provides shape measurement over the length of the sensor. In contrast to a discrete position sensor, a shape sensor enables shape measurement via a single sensor. Note that a shape sensor may include a single continuous sensing region or multiple sensing regions distributed over the length of the sensor, so long as the data from the shape sensor as a whole can be used to determine the measured shape. The integrated nature of a shape sensor can be particularly useful in delivering accurate shape measurement of needle 110. This in turn can enable more precise control and/or enhanced error correction to ensure that needle 110 accurately traverses a desired surgical trajectory.

Note that although shape sensor 120 is depicted and described as a single shape sensor for explanatory purposes, in various embodiments shape sensor 120 can include multiple shape sensors, where each shape sensor measures the shape of a continuous portion of the overall length of needle 110. Also, in various other embodiments, needle 110 can include multiple parallel shape sensors, as indicated by optional additional shape sensor(s) 120-2. Such multiple shape sensors can be used, for example, to provide for greater shape modeling precision or to compensate for temperature or other sensor-affecting factors. Various other usages will be readily apparent.

Figures 3A, 3B, 3C:
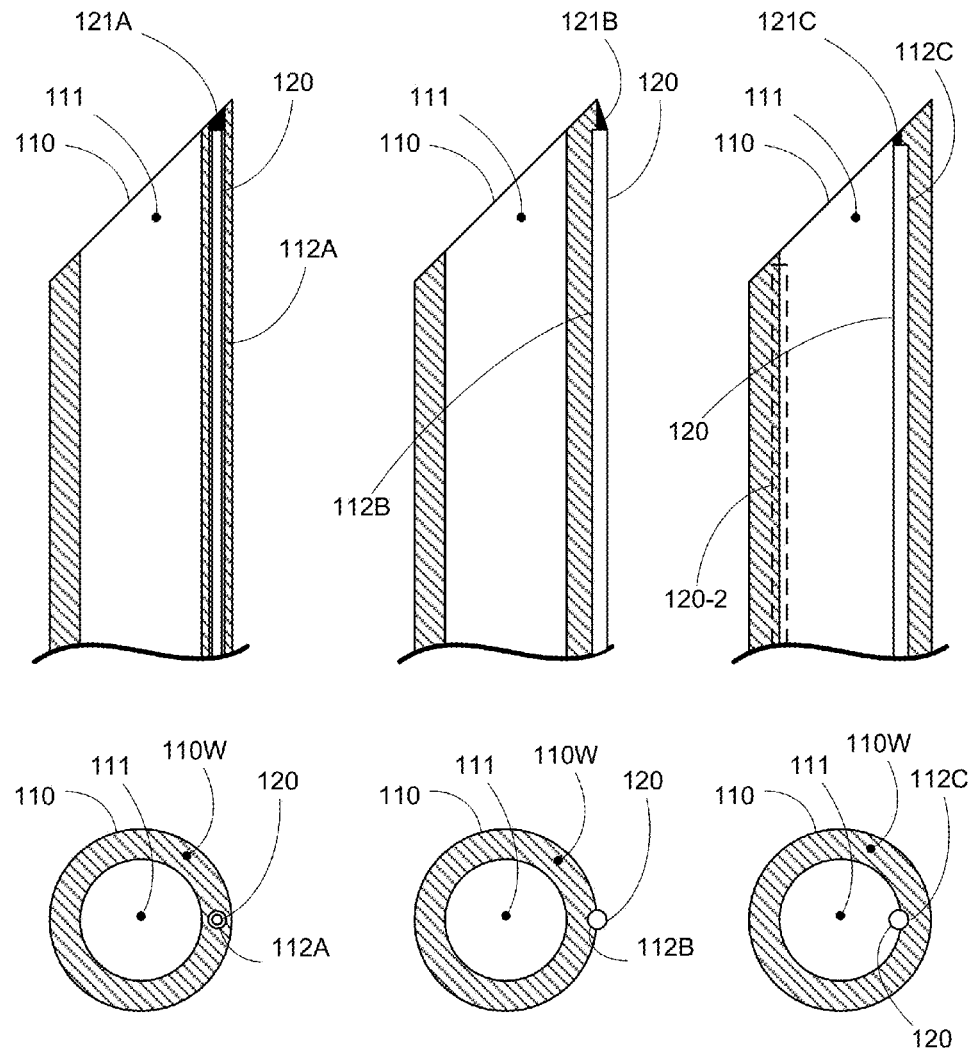
FIGS. 3A-3F are various steerable needle/shape sensor combinations usable with the minimally invasive surgical system of FIG. 1A.

Shape sensor 120 can be coupled to needle 110 in a variety of ways. For example, FIG. 3A shows shape sensor 120 housed in a lumen 112A in a wall 110W of needle 110. Wall 110W further defines an interior needle lumen 111 for surgical use (e.g., material delivery or biopsy). In various embodiments, an optional securing feature 121A (e.g., a slot, ridge, threads, shoulder, or any other feature) can be provided on needle 110 (e.g., at the distal end region or anywhere along lumen 112A) to assist in securing, aligning, and/or orienting sensor 120 with needle 110. In such embodiments, shape sensor 120 can itself include a corresponding mating feature(s).

FIG. 3B shows another embodiment of needle 110 in which shape sensor 120 is attached to the outer surface of wall 110W. In some embodiments, wall 110W can include an optional outer groove 112B that can help to capture and/or align sensor 120 with needle 110. In various other embodiments, an optional securing feature 121B (e.g., a slot, ridge, threads, shoulder, or any other feature) can be provided on needle 110 (e.g., at the distal end region or anywhere along groove 112B) to assist in securing, aligning, and/or orienting sensor 120 with needle 110. In such embodiments, shape sensor 120 can itself include a corresponding mating feature(s).

FIG. 3C shows another embodiment of needle 110 in which shape sensor 120 is attached to the inner surface of wall 110W. In some embodiments, wall 110W can include an optional inner groove 112C that can help to capture and/or align sensor 120 with needle 110. In various other embodiments, an optional securing feature 121C (e.g., a slot, ridge, threads, shoulder, or any other feature) can be provided on needle 110 (e.g., at the distal end region or anywhere along groove 112C) to assist in securing, aligning, and/or orienting sensor 120 with needle 110. In such embodiments, shape sensor 120 can itself include a corresponding mating feature(s).

Note that in various other embodiments, multiple shape sensors 120 can be incorporated into needle 110. For example, and shown in FIG. 1A, an optional second shape sensor 120-2 can be affixed to needle 110 to provide additional shape measurement data for enhanced accuracy, error correction, temperature compensation, etc. Note that while both sensors are depicted as being positioned within inner lumen 111 of needle 110 for exemplary purposes, in various other embodiments, both shape sensors 120 can be on the outer surface of needle 110, or within wall 110W, or in any combination of inner surface, outer surface, and in-wall placements. Note further that any number of shape sensors 120 can be present, and in any relative arrangement along needle 110.

Figure 3D:
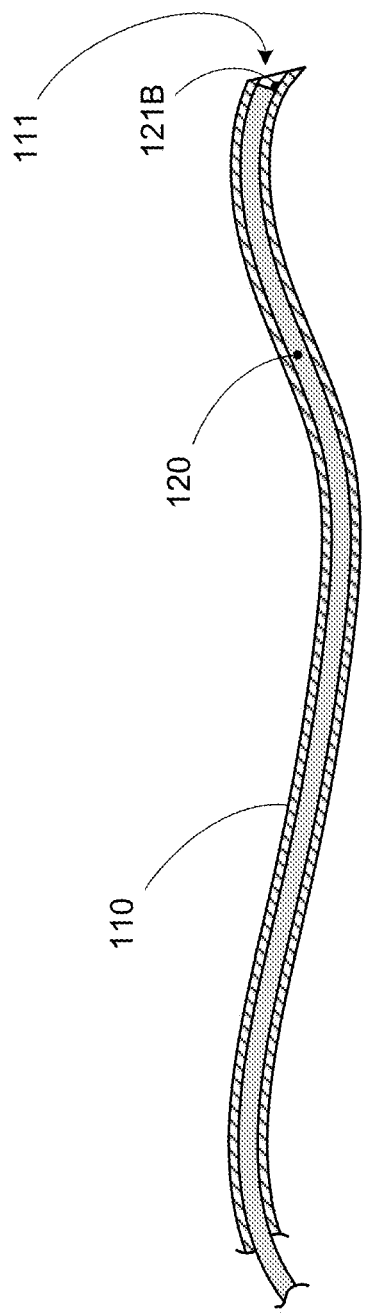

FIG. 3D shows another embodiment of needle 110 in which shape sensor 120 is positioned within needle lumen 111. This configuration allows shape measurements of needle 110 to be taken during insertion and navigation until the surgical target location is reached. Shape sensor 120 can then be removed, as shape and position information is no longer required, and the surgical procedure can be performed using the (now clear) needle lumen 111. In various embodiments, shape sensor 120 can be replaced within needle lumen 111 prior to removal of needle 110 from the patient. In some embodiments, shape sensor 120 can be part of a flexible stylet or guidewire sized to fit within needle lumen 111. The placement of shape sensor 120 within needle lumen 111 beneficially avoids impact to needle wall 110W and can allow for the use of larger diameter and potentially more accurate shape sensors 120.

Figure 3E:
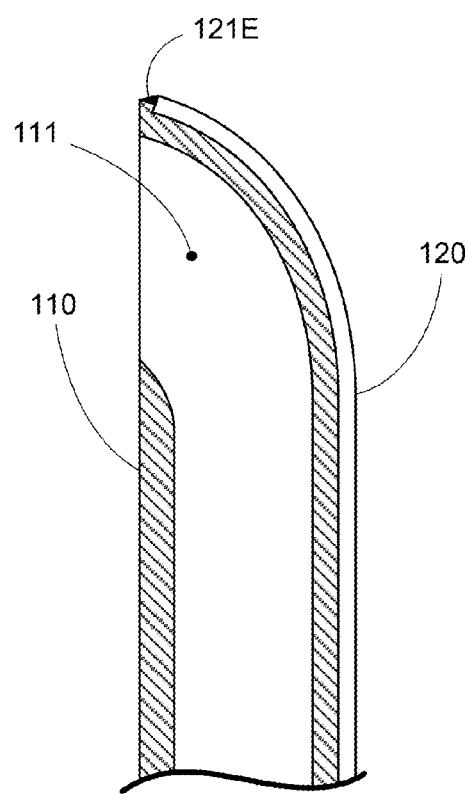
Figure 3F:
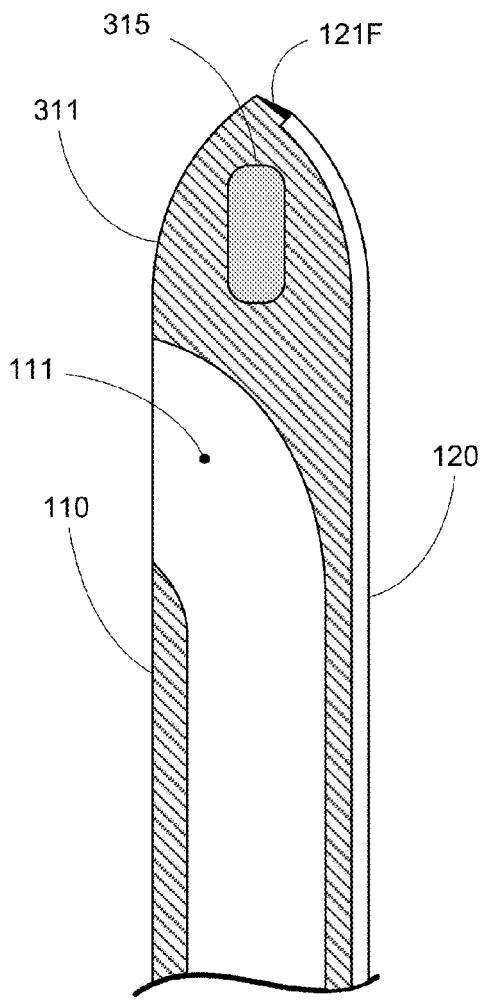

Note further that the tip design for steerable needle 110 can take any form or shape as required for the particular procedural requirements of a surgical procedure. In some embodiments, needle 110 can include a bevel tip (e.g., Baker needle tip), as shown in FIGS. 3A-3D. In various other embodiments, alternative tip geometries can be used. For example, FIG. 3E shows needle 110 with a rounded tip (e.g., Tuohy needle tip), and FIG. 3F shows needle 110 with a solid tip (e.g., Sprotte needle tip). Various other tip designs will be readily apparent.

As further shown in FIG. 3F, in some embodiments needle 110 can include optional additional sensors 315 to provide further usage information. For example, sensor 315 can be a position sensor (e.g., EM sensor, accelerometer, etc.) providing localized position data that can be used with the shape data from shape sensor 120 to model the in-situ pose and/or shape of needle 110. Although depicted in the solid distal tip 311 of needle 110 in FIG. 3F for exemplary purposes, in various other embodiments, additional sensor(s) 315 can be located anywhere on needle 110, regardless of specific needle configuration.

Likewise, various mechanisms can be used to steer needle 110. For example, depending on the shape and mechanical properties of needle 110, interaction forces between needle 110 and the patient anatomy (i.e., the target tissue and/or any intervening anatomy between the surgical entry point and the target tissue) can cause needle 110 to deflect as it is advanced through that patient anatomy. The mechanism may be actuated, manually or automatically, using information from the shape sensor as input.

For example, in various embodiments, needle 110 can be made from a highly flexible material (e.g., nitinol) and have an asymmetric bevel tip or pre-bent tip, such as shown in FIG. 1A. When inserted into tissue, the bevel tip will cause needle 110 to move in a curved trajectory in the direction of the bevel. Steerability is provided by rotating needle 110 axially to cause the bevel direction, and hence the needle trajectory, to change. In such cases, actuator 130 can be anything from a knob(s), handle(s), or other manual interface, to active drivers such as a servo motor, or combinations of manual and automated actuators.

Figure 2A:
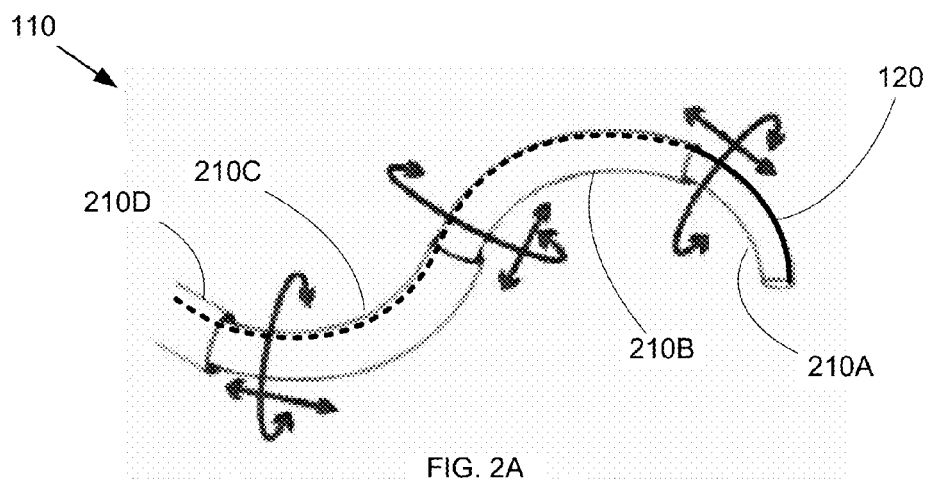
FIGS. 2A-2B are diagrams of steerable needle types usable with the minimally invasive surgical system of FIG. 1A.
Figure 2B:
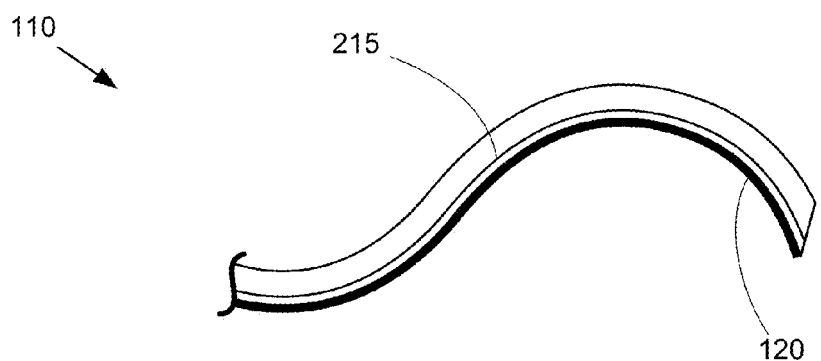

In various other embodiments, needle 110 can be steered via more active mechanisms. For example, FIG. 2A shows an embodiment of needle 110 formed from multiple coaxial curved needle segments 210A, 210B, 210C, and 210D. Note that while four needle segments 210 are depicted for exemplary purposes, in various other embodiments needle 110 can include any number of segments. In use, actuator 130 can control the relative rotation and extension of segments 210A-210D, thereby determining the shape and orientation of needle 110. FIG. 2B shows another embodiment of needle 110 in which one or more control cables 215 are provided to which tension and/or extension forces can be applied to cause desired bending of needle 110. Cable(s) can be controlled via mechanical tensioners, motor actuators, or any other mechanism. For example, in some embodiments, cable(s) 215 can include material that responds to thermal changes, such as nitinol wire(s) configured to contract in response to electrical current-induced heating (such as described in "A Nitinol Wire Actuated Stewart Platform", by Dunlop et al. (Proc. 2002 Australasian Conference on Robotics and Automation, Nov. 27-29, 2002), herein incorporated by reference in its entirety). Various other steering mechanisms will be readily apparent.

Regardless of the specific steering mechanism used with flexible needle 110, the usability of system 100 in a minimally invasive surgical procedure is enhanced by the inclusion of shape sensor 120 and the shape information provided therefrom. Furthermore, such benefit accrues regardless of the particular mode of control applied to needle 110. Specifically, in various embodiments, system 100 can be a purely manual system (e.g., an endoscopic instrument), in which actuator 130 is directly controlled by an optional manual controller 150, as shown in FIG. 1A. In some embodiments, optional manual controller 150 can be actuator 130 (e.g., a knob, handle, or grip for rotating needle 110), and in other embodiments optional manual controller can be a handle(s), trigger(s), lever(s), grip(s), and/or any other user interface for providing control inputs to actuator 130, either via direct mechanical attachment or linkage, via electrical/electronic control, or any combination of the above. In various other embodiments, system 100 can be a robotic system in which control over needle 110 is provided via a console or other remote interface of an optional robotic platform 160. In yet other embodiments, system 100 can incorporate elements of both direct control and robotic control (e.g., robotic system with manual override) and therefore include both optional manual controller 150 and optional robotic platform 160.

In robotically-assisted or telerobotic surgery, the surgeon typically operates a control device to control the motion of surgical instruments at the surgical site from a location that may be remote from the patient (e.g., across the operating room, in a different room or a completely different building from the patient) or immediately adjacent to the patient. Thus in some embodiments, robotic platform 160 can include one or more manually-operated input devices, such as joysticks, exoskeleton gloves or the like, which are coupled (directly or indirectly) to actuator 130 with servo motors or other drive mechanisms for steering needle 110 to the surgical site. During a procedure, robotic platform 160 can, in some embodiments, provide mechanical articulation and control of a variety of surgical instruments in addition to needle 110, such as tissue graspers, electrosurgical cautery probes, retractors, staplers, vessel sealers, endoscopes, scalpels, ultrasonic shears, suction/irrigation instruments, and the like, that each perform various functions for the surgeon, e.g., grasping a blood vessel, or dissecting, cauterizing or coagulating tissue.

Shape sensor 120 can be any type of shape sensor capable of measuring the curvature of flexible needle 110 during surgical use. For example, in various embodiments, shape sensor 120 can include a fiber optic shape sensor, such as described with respect to the systems and methods for monitoring the shape and relative position of a optical fiber in three dimensions described in U.S. patent application Ser. No. 11/180,389, filed on Jul. 13, 2005; U.S. provisional patent application Ser. No. 60/588,336, filed on Jul. 16, 2004, and U.S. Pat. No. 6,389,187, filed on Jun. 17, 1998, the disclosures of which are incorporated herein in their entireties. In some embodiments, an optical fiber in shape sensor 120 can comprise one or more cores (either single- and/or multi-mode) contained within a single cladding. Multi-core constructions can be configured to provide sufficient distance and cladding separating the cores such that the light in each core does not interact significantly with the light carried in other cores. In other embodiments, shape sensor 120 can include any number of optical fibers with the same or varying numbers of cores. In other embodiments, one or more of the cores in the optical fiber can be used for illumination and/or ablation.

In certain embodiments, shape sensor 120 can be a fiber optic bend sensor that includes a backscatter mechanism such as fiber Bragg gratings (FBGs), such as in product from Luna Innovations, Inc. (Blacksburg, Va.). In such embodiments, an array of FBGs can be provided within each core that comprises a series of modulations of the core's refractive index so as to generate a spatial periodicity in the refraction index. The spacing may be chosen so that the partial reflections from each index change add coherently for a narrow band of wavelengths, and therefore reflect only this narrow band of wavelengths while passing through a much broader band. During fabrication of the FBGs, the modulations are spaced by a known distance, thereby causing reflection of a known band of wavelengths. However, when a strain is induced on the fiber core, the spacing of the modulations will change, depending on the amount of strain in the core.

To measure strain, light is sent down the fiber, and the reflected wavelength is a function of the strain on the fiber and its temperature. This FBG technology is commercially available from a variety of sources, such as Smart Fibres Ltd. of Bracknell, England. When applied to a multicore fiber, bending of the optical fiber induces strain on the cores that can be measured by monitoring the wavelength shifts in each core. By having two or more cores disposed off-axis in the fiber, bending of the fiber induces different strains on each of the cores. These strains are a function of the local degree of bending of the fiber. Regions of the cores containing FBGs, if located at points where the fiber is bent, can thereby be used to determine the amount of bending at those points. These data, combined with the known spacings of the FBG regions, can be used to reconstruct the shape of the fiber.

Note, however, that while the use of FBGs are described above for exemplary purposes, any mechanism for creating backscatter could be used in shape sensor 120, such as Rayleigh scattering, Raman scattering, Fluorescence scattering, and Brillouin scattering, among others. Typically, fiber optic shape sensors operate via optical time domain reflectometry (OTDR) or via optical frequency domain reflectometry (OFDR). The Kerr effect can also be used in shape sensor 120.

Note further that in various other embodiments, any flexible, elongate sensor or combination of sensors can be used as shape sensor 120. In various embodiments, shape sensor 120 can include a bend-enhanced fiber (BEF) sensor, such as ShapeTape from Measurand Inc. (Fredericton, New Brunswick, Canada), flexible piezoresistive sensor arrays or wire strain detectors (such as described in "ULTRA-SENSITIVE SHAPE SENSOR TEST STRUCTURES BASED ON PIEZO-RESISTIVE DOPED NANOCRYSTALLINE SILICON", Alpuim et al. (NanoSpain 2008, Apr. 14-18, 2008), herein incorporated by reference in its entirety, and in "Electromechanical analysis of a piezoresistive pressure microsensor for low-pressure biomedical applications", Herrera-May et al. (REVISTA MEXICANA DE FI'SICA 55 (1) 14-24 Feb. 2009), herein incorporated by reference in its entirety), a nitinol wire for resistive strain measurement, an unaltered polarization-maintaining (PM) optical fiber, and/or any other shape sensing technologies.

Figure 1B:
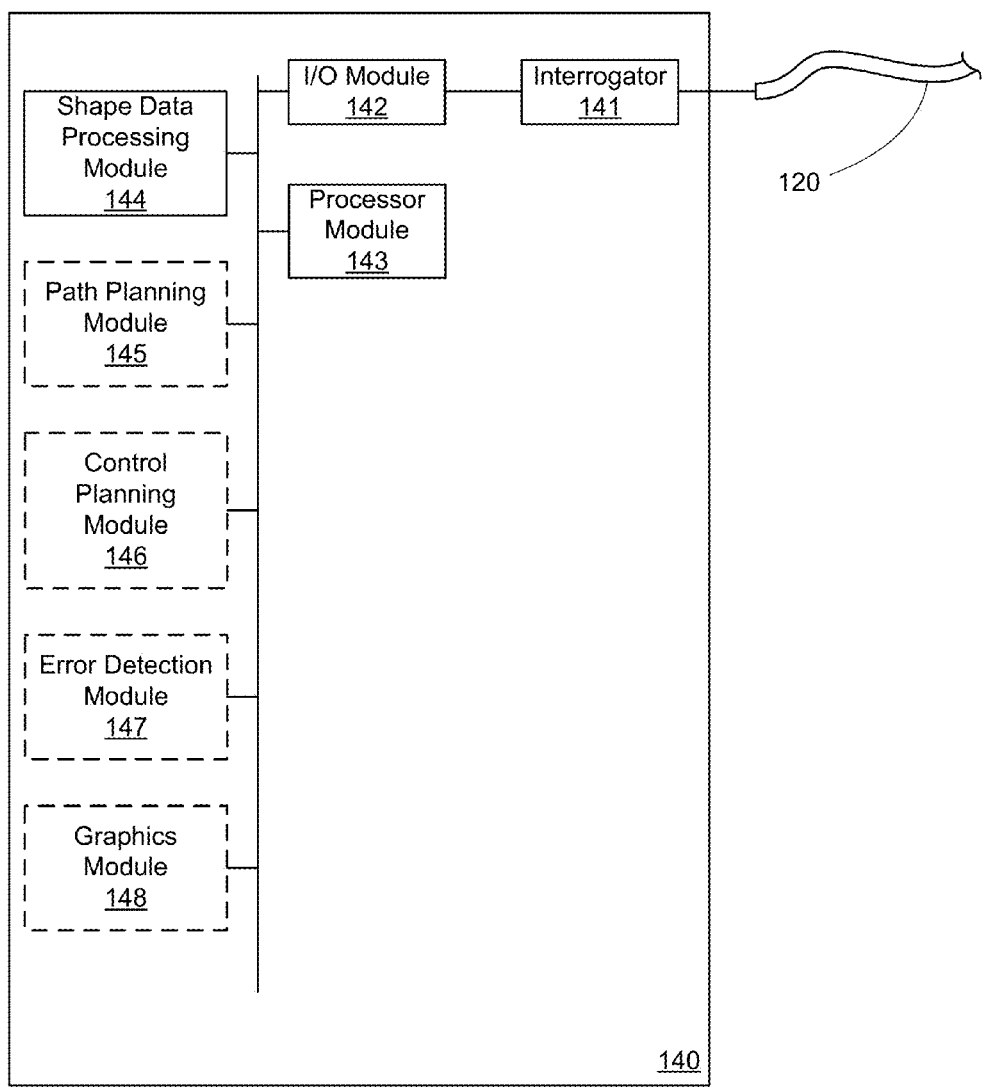
FIG. 1B is a block diagram of a shape sensor processing system that can be part of the minimally invasive surgical system of FIG. 1A.

Processor 140 detects the shape and position of steerable needle 110 and processes that information to assist in surgical procedures. Processor 140 is configured to interface with the specific type of sensor(s) in shape sensor 120 (e.g., providing interferometry and/or reflectometry capabilities for use with optical fiber sensors, or providing a voltage and/or current meter for use with resistance-based sensors). FIG. 1B shows an exemplary embodiment of processor 140 for processing the measurement data from a fiber optic shape sensor 120. In view of this disclosure, instructions and modules used in any one of, or any combination of operations described with respect to processor 140 can be implemented in a wide variety of software and/or hardware architectures, such as software code modules running on dedicated processors, application specific integrated circuits (ASICs), field programmable gate arrays (FPGAs), or any other logic implementation, alone or in any combination.

Processor 140 in FIG. 1B includes an interrogator 141, an input/output module 142, a processor module 143, and a shape data processing module 144. Interrogator 141 interrogates the optical fiber of shape sensor 120 and provides shape information to input/output module 142. Processor module 143 then processes the information from input/output module 142 using a shape data processing module 144 (e.g., stored in memory within processor 140). The generated shape information for needle 110 can then be used to model the in-situ pose and/or shape of needle 110. In some embodiments, known reference frame data (e.g., the position and orientation of actuator 130/proximal end region of needle 110) can be combined with the shape information for needle 110 to determine the in-situ pose and/or shape. In various other embodiments, positional measurements taken of needle 110 (e.g., via additional sensors on needle 110 or through visualization tracking) can be used with the shape data from shape sensor 120 to determine the in-situ pose and/or shape. More detailed description of an exemplary pose-determination process is provided in copending and commonly assigned U.S. patent application Ser. Nos. 12/164,829, and 12/618,082, both of which are incorporated herein by reference in their entireties.

Note that in various embodiments, processor 140 (or system 100) can include optional additional processing modules to make use of the shape data provided by shape sensor 120. In some embodiments, an optional path planning module 145 can be included to identify an appropriate trajectory (or multiple trajectory options) for either fully- or semi-automated control or for providing guidance for manual control over system 100. In various other embodiments, if automated or semi-automated control is provided by system 100, an optional control planning module 146 can be included to generate the appropriate control signals for actuator 130, for example based on the output of path planning module 145.

In various other embodiments, an optional error detection module 147 can be included to compare measured shape, pose, and/or position data against expected values (e.g., desired values or values predicted from a mathematical model). For example, in some embodiments, the measured data can be compared against model data to validate and/or update the model data. In other embodiments, the measured data can be compared to target data (e.g., comparing actual trajectory of needle 110 to a desired trajectory) to avoid excessive deviation from a desired behavior. In some embodiments, such error detection can provide notification to the surgeon via visual, aural, or tactile cues or reports. In various other embodiments, deviations can be presented graphically (e.g., on a video monitor, overlaying actual trajectory onto desired trajectory). In such embodiments, an optional graphics module 148 can also be included in processor 140 to provide the necessary graphical representation of the measurements of shape sensor 120. In other embodiments, graphics module 148 can be included simply to provide a visual representation of the shape data measured by shape sensor 120.

As noted above, a surgical procedure can be beneficially enhanced by measuring the shape of a steerable needle and then controlling the needle (e.g., adjusting the shape of the needle, changing the orientation of the needle (e.g., axial rotation), advancing/retracting the needle, etc.) based on that measured shape. Note that while the descriptions herein refer to the use of a steerable flexible needle with shape sensor in surgical applications for exemplary purposes, in various embodiments, the same methods and procedures can be use in animals (e.g., veterinary use), cadavers, artificial anatomic replicas, and/or computer simulations of surgical procedures.

Figure 4:
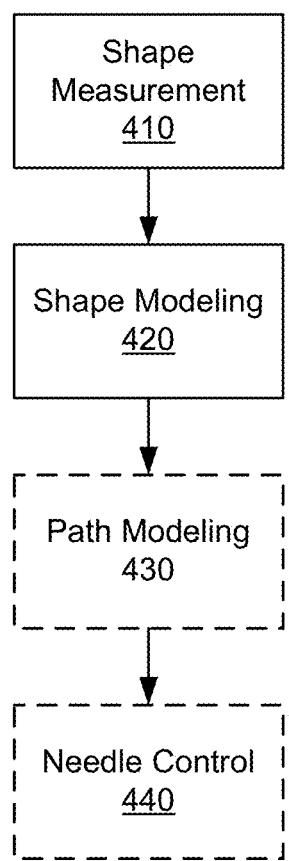
FIGS. 4-7 are operational flow diagrams for a minimally invasive surgical system incorporating a steerable needle with shape sensor.

FIG. 4 shows an exemplary flow diagram for the use of shape sensing in such a procedure. In a Shape Measurement step 410, the shape of a steerable flexible needle (such as needle 110 described above) is measured. The measurement can be performed using any type of shape sensor capable of providing real time shape information for the flexible needle (such as shape sensor 120 described above). Then, in a Shape Modeling step 420, the measured data is used to model the actual shape of the flexible needle.

Note that depending on the requirements of the surgical system and procedure itself, the specific level of shape modeling in step 420 can vary. For example, in some embodiments, step 420 may simply involve determining the standalone shape of the needle—for example to determine if the needle has reached a desired deployed state. In some other embodiments, step 420 can involve determining the shape of the needle along with its orientation (e.g., using additional reference frame information from the proximal (attachment) region of the needle to the actuator (such as actuator 130, above), or from additional sensor data (such as sensor 315 above)). For example, FIG. 5 shows an embodiment of the flow diagram of FIG. 4 that includes an optional Pose Modeling step 522.

The continuous shape modeling of step 420 can provide a significant procedural advantage over approaches limited to the use of catheters having a single position sensor (or several discrete sensors at particular locations), which can only estimate shape and orientation by assuming perfect mechanical transfer between the inputs and the measured locations. The actual shape measurements of step 420 can allow total insertion depth of the needle to be accurately determined, along with distal tip position and orientation. This determination can be made regardless of the torsional and axial flexibility of the needle and any effects of friction and normal forces between the needle and the patient tissue, which would otherwise need to be precisely modeled to produce similar results using a discrete sensor system—an unwieldy and likely unmanageable approach for most surgical applications.

Figure 5:
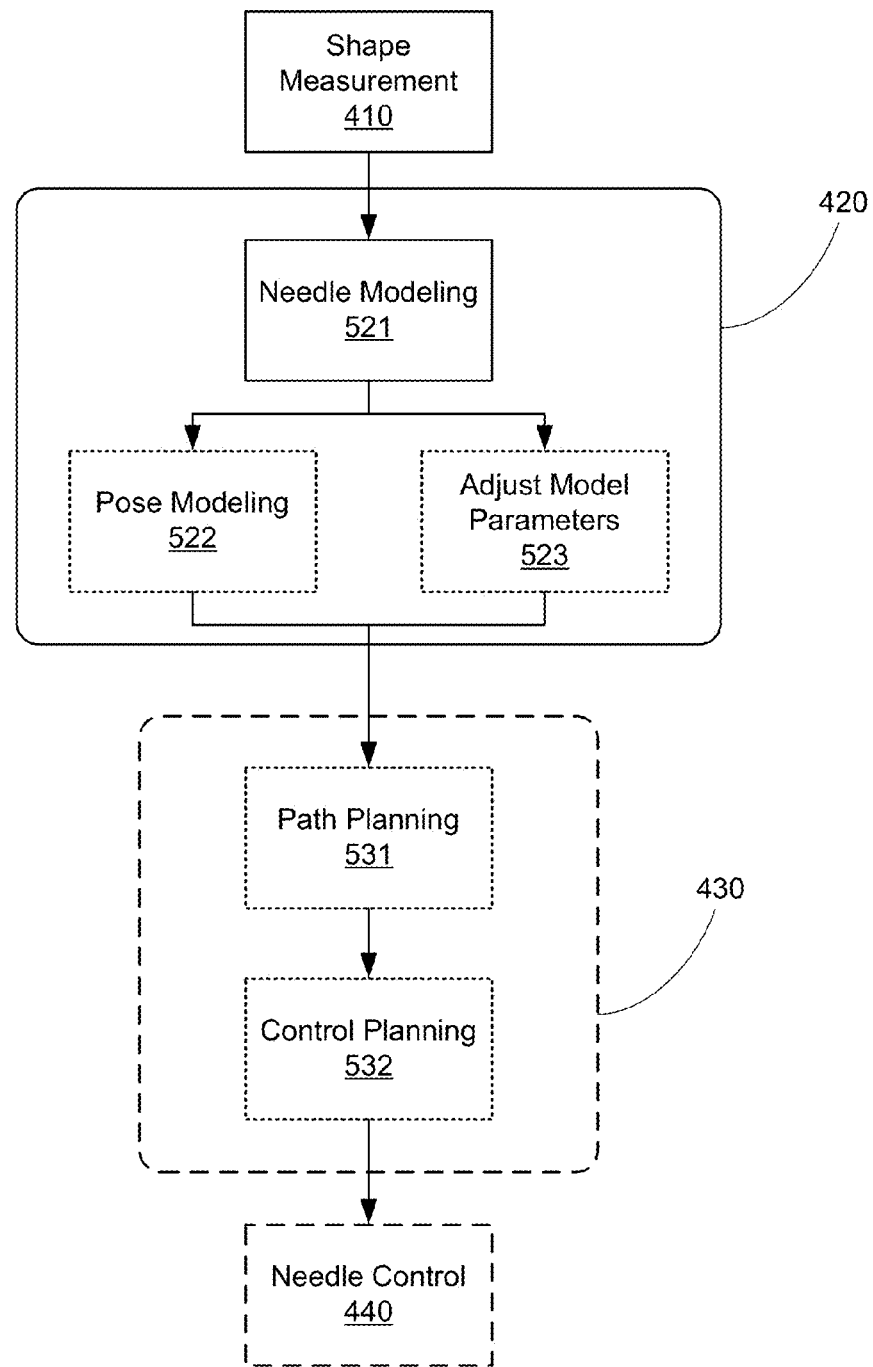

In some embodiments, step 420 can include the identification or refinement of model parameters in a biomechanical model of the tissue and/or kinematic model of the needle system, as indicated by optional Adjust Model Parameters step 523 in FIG. 5. For example, the actual behavior of the needle (e.g., bend radius) as it traverses a patient tissue or anatomical structure can be used to derive tissue density, changes in material (e.g., diseased or degenerative tissue regions exhibiting unexpected material properties, such as tumors, cysts, osteoporosis, etc.), or other difficult to predict and model anatomical aspects. In other embodiments, the actual needle trajectory can be used to estimate and update kinematic mapping between the actuator inputs and the actual needle movement (e.g., the tip and/or the shaft of the needle), thereby improving the responsiveness and accuracy of the needle control. In other embodiments, the actual needle trajectory can be used to calculate loading of the needle, at discrete locations or along its entire length, since the curvature(s) of the needle will be dependent at least in part on the local forces applied to the needle.

In some other embodiments, the pose information determinable in step 420 can be beneficially used to indicate or visualize the actual placement of the needle within a patient or the actual surgical trajectory being followed by the needle, as in an optional Path Modeling step 430. For example, step 430 can include using the needle shape information determined in step 420 to determine one or more target trajectories for the continuing advance of the needle (e.g., based on needle properties, anatomical model properties, needle behavior up to current location, supplemental anatomical information (e.g., visualization, enhanced material properties based on actuation force required by needle, etc.), and/or any other path-affecting information), as indicated by an optional Path Planning step 531 in FIG. 5.

Figure 6:
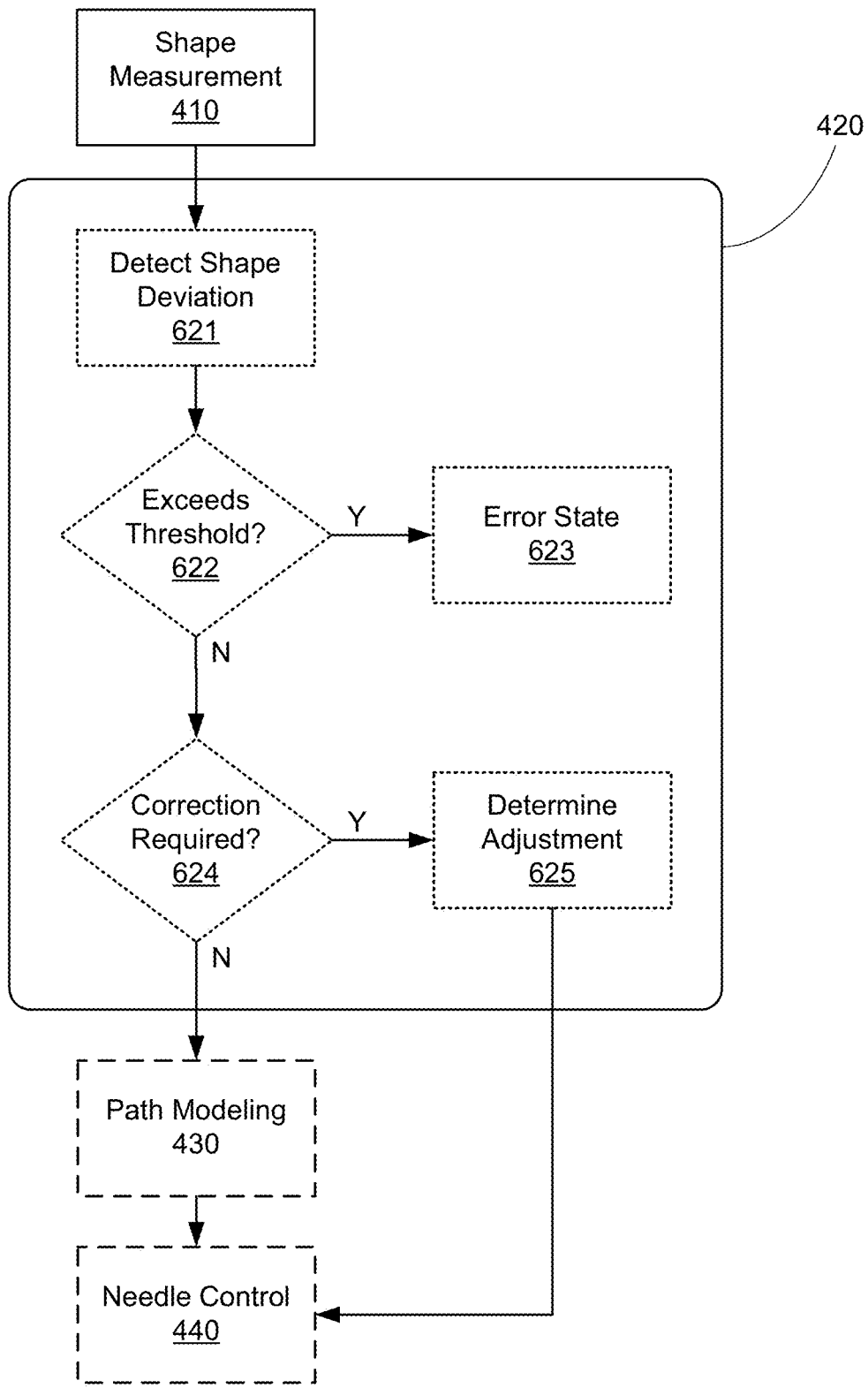

In various other embodiments, steps 420 and/or 430 can include comparing the actual needle shape and/or trajectory with an expected or desired shape/trajectory. Any deviation from the desired shape/trajectory can be identified and/or used to provide feedback to the surgeon as to potential corrective actions, depending on the magnitude of the deviation. For example, FIG. 6 shows a flow diagram in which step 420 includes an optional Detect Shape Deviation step 621 in which the measured shape is compared to an expected shape. The deviation can then be assessed in an Exceeds Threshold? step 622, where if the deviation is greater than some preset limit, a notification is provided in an Error State step 623. This notification can take any form, including a visual warning, an audible warning, an error message, a tactile indication, warning icon, and/or system freeze/recovery action, among others. In some embodiments, step 623 can result in procedure abort or restart, due to excessive needle deformation. In various other embodiments, if the shape deviation is less than a maximum deviation, a determination is made in an optional Correction Required? step 624, wherein if the deviation is small enough, no adjustment to the needle shape is made, and the process simply continues. However, if the deviation is determined to require correction, such correction can be calculated in a Determine Adjustment step 625. This adjustment can be provided to the surgeon as instructions, graphical representation, or any other means for conveying the information to the surgeon, or can be provided automatically to the system to cause automatic correction of the needle shape (e.g., providing appropriate control signals to the needle actuator).

Figure 7:
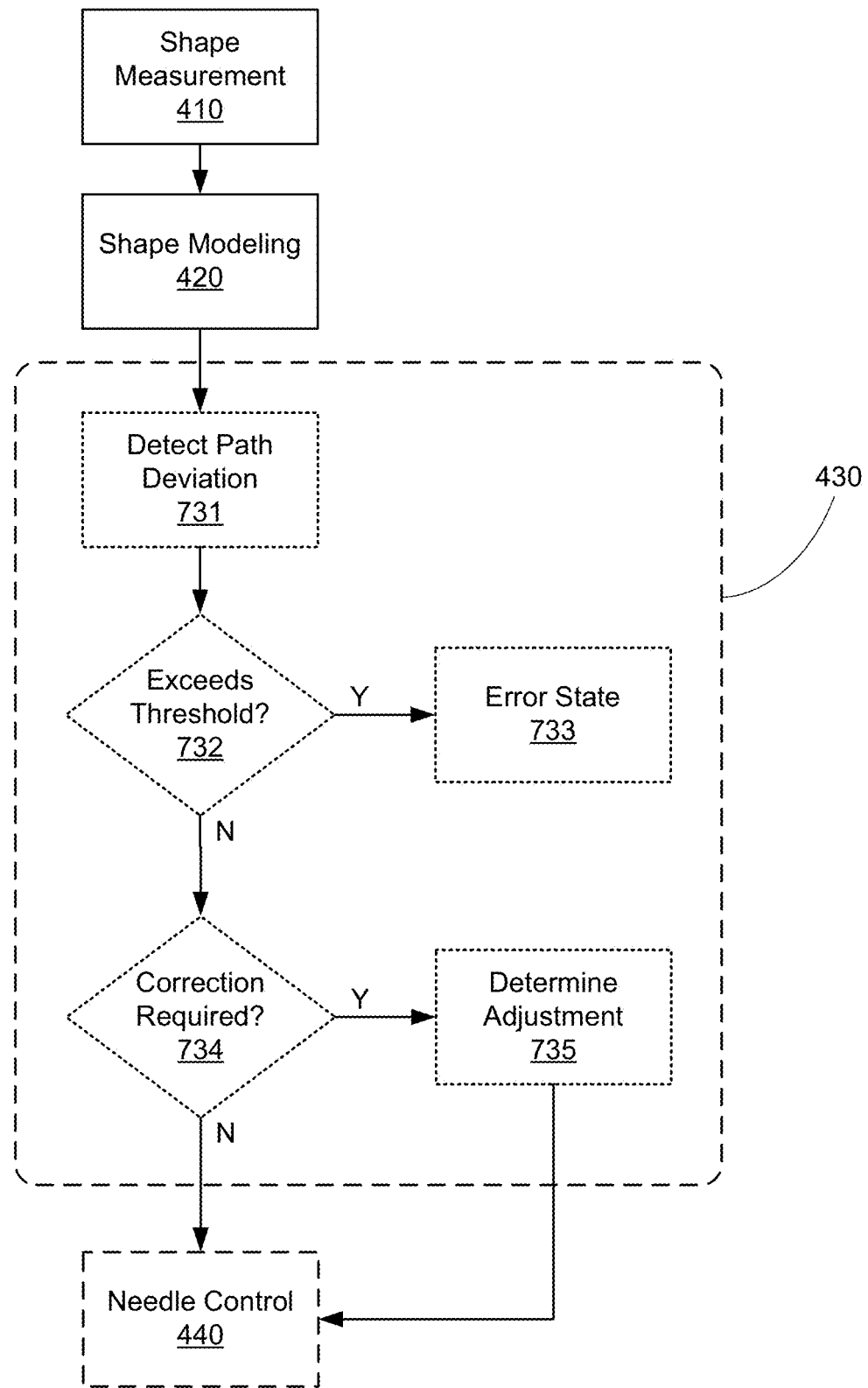

In another example, FIG. 7 shows a flow diagram in which step 430 includes an optional Detect Path Deviation step 731 in which the measured needle trajectory is compared to an expected trajectory (e.g., a pre-operatively determined trajectory or an intraoperatively modeled trajectory). The deviation can then be assessed in an Exceeds Threshold? step 732, where if the deviation is greater than some preset limit, a notification is provided in an Error State step 733. This notification can take any form, including a visual warning, an audible warning, an error message, a tactile indication, warning icon, and/or system freeze/recovery action, among others. In some embodiments, step 733 can result in procedure abort or restart, due to excessive trajectory deviation. In various other embodiments, if the trajectory deviation is less than a maximum deviation, a determination is made in an optional Correction Required?

step 624, wherein if the deviation is small enough, no adjustment to the needle shape and/or actuation control inputs is made, and the process simply continues. However, if the deviation is determined to require correction, such correction can be calculated in a Determine Adjustment step 625. This adjustment can be provided to the surgeon as instructions, graphical representation, or any other means for conveying the information to the surgeon, or can be provided automatically to the system to cause automatic correction of the needle trajectory (e.g., providing appropriate control signals to the needle actuator).

In some other embodiments, the shape and/or position of the needle can also be adjusted in an optional Needle Control step 440. For example, the shape and/or path information derived from step 420 and optional step 430, respectively, can be used to determine the appropriate advancement/retraction and/or shape adjustment for the needle. For instance, if steps 420 and/or 420 indicate that the needle shape is sub-optimal for completion of the desired procedure, the needle can be adjusted towards a more optimized shape in step 440 (e.g., by actively changing the needle shape, by changing the needle orientation to cause the desired shape change during advancement/retraction, and/or by performing any other shape-affecting action). Similarly, if steps 420 and/or 430 indicate that the trajectory of the needle is sub-optimal for completion of the desire procedure, the needle can be adjusted towards a more optimized path in step 440 (e.g., by changing needle shape, by changing the needle orientation (e.g., rotation), retracting the needle, and/or any other trajectory-impacting action). In various embodiments, this shape and/or trajectory adjustment can be performed manually, in response to surgeon cues (e.g., visual indication of deviation, sounds, or tactile indications when a deviation from the desired path is detected), automatically, or any combination of the above. In some embodiments, the specific controls applied to the needle actuator can be determined based on the shape sensor data, as indicated by an optional Control Planning step 532 in FIG. 5.

All examples and illustrative references are non-limiting and should not be used to limit the claims to specific implementations and embodiments described herein and their equivalents. The headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the disclosure, even though not specifically shown in the drawings or described in the text.

The invention claimed is:

1. A flexible needle comprising:
a flexible elongate needle body with a channel and a needle lumen extending therein, the needle lumen defined by an interior surface of a wall of the flexible elongate needle body, the channel extending within the wall, the flexible elongate needle body including a distal tip portion, wherein the distal tip portion of the flexible elongate needle body is configured to pierce or puncture target tissue, wherein the channel comprises a groove;
a shape sensor coupled to the flexible elongate needle body, wherein the shape sensor extends into the distal tip portion of the flexible elongate needle body and wherein the shape sensor is at least partially positioned within the groove; and
a connector adapted for connecting the shape sensor to a processor for determining the shape of the flexible elongate needle body based on data from the shape sensor.

2. The flexible needle of claim 1 wherein the shape sensor comprises at least one of an optical fiber, a fiber Bragg grating, a nitinol wire, and a piezoresistive element.

3. The flexible needle of claim 1 wherein the shape sensor is attached to the wall.

4. The flexible needle of claim 1, wherein the needle lumen has an opening in the distal tip portion, the shape sensor extending beyond a portion of the opening.

5. The flexible needle of claim 1, wherein the groove comprises one or more positioning features mated with the shape sensor and wherein the one or more positioning features prevents movement of the shape sensor along the groove.

6. The flexible needle of claim 1, wherein the distal tip portion is not moveable relative to the flexible elongate needle body.

7. The flexible needle of claim 1, wherein the flexible elongate needle body includes a plurality of concentric curved segments, wherein each of the plurality of concentric curved segments is independently rotatable and extendible and wherein a most distal segment of the plurality of concentric curved segments includes the distal tip portion configured to pierce or puncture target tissue.

8. The flexible needle of claim 1 further comprising at least one control cable, wherein flexion of the flexible elongate needle body is controlled by the control cable.

9. The flexible needle of claim 1 wherein the distal tip portion comprises one of a bevel tip, a curved tip, and a solid tip that terminates at a point configured to pierce or puncture target tissue.

10. The flexible needle of claim 1, further comprising a second shape sensor, at least a portion of the second shape sensor being substantially parallel to at least a portion of the shape sensor, wherein the connector is further adapted for connecting the second shape sensor to the processor for determining the shape of the flexible needle based on data from the shape sensor and the second shape sensor.

11. The flexible needle of claim 1, wherein the distal tip portion forms a solid needle tip and wherein the flexible needle further comprises a position sensor disposed within the solid needle tip, wherein the connector is further adapted for connecting the position sensor to the processor for determining a position of a section of the flexible needle based on data from the position sensor.

12. A flexible needle comprising:
a flexible elongate needle body with a needle lumen extending therein, the needle lumen defined by an interior surface of a wall of the flexible elongate needle body, the flexible elongate needle body including a distal tip portion, wherein the distal tip portion of the flexible elongate needle body is configured to pierce or puncture target tissue, the flexible elongate needle body further including a second lumen defined between the interior surface of the wall and an exterior surface of the wall;
a shape sensor coupled to the flexible elongate needle body, wherein the shape sensor extends into the distal tip portion of the flexible elongate needle body, wherein the shape sensor is positioned at least partially within the second lumen; and a connector adapted for connecting the shape sensor to a processor for determining the shape of the flexible elongate needle body based on data from the shape sensor.

13. The flexible needle of claim 12 wherein the second lumen comprises a cylindrical interior lumen extending within the wall, wherein the shape sensor is removably insertable into the cylindrical interior lumen.

14. A surgical system comprising:
   a flexible needle including:
      a flexible elongate needle body including a needle lumen extending therein, wherein the flexible elongate needle body includes a distal region configured to pierce or puncture target tissue and wherein the needle lumen terminates in an opening in the distal region, and wherein the flexible elongate needle body comprises a wall defining the needle lumen, the wall comprising a groove,
      a shape sensor extending along a length of the flexible elongate needle body and extending beyond a portion of the opening, wherein the shape sensor is attached to the wall and at least partially positioned within the groove, and
      a connector adapted for connecting the shape sensor to a processor; and
   an actuator for manipulating the flexible needle.

15. The surgical system of claim 14 further including the processor for determining a shape of the flexible needle based on data from the shape sensor.

16. The surgical system of claim 14, wherein the shape sensor comprises at least one of an optical fiber having a fiber Bragg grating, a nitinol wire, and a piezoresistive element.

17. The surgical system of claim 14, wherein the flexible elongate needle body comprises a wall defining an interior lumen and wherein the shape sensor is removably insertable into the interior lumen.

18. The surgical system of claim 17, wherein the shape sensor comprises a stylet sized to fit within the interior lumen.

19. The surgical system of claim 14, wherein the shape sensor is attached to an external surface of the wall.

20. The surgical system of claim 14, wherein the shape sensor is attached to an internal surface of the wall.

21. The surgical system of claim 14, wherein the groove comprises one or more positioning features mated with the shape sensor, wherein the one or more positioning features prevents movement of the shape sensor along the groove.

22. The surgical system of claim 21, wherein the one or more positioning features comprises at least one of a slot, a ridge, and a threaded section.

23. The surgical system of claim 14, wherein the flexible elongate needle body comprises a wall having an interior surface and an exterior surface, the interior surface defining the needle lumen, wherein a second lumen is defined between the interior surface and the exterior surface, and wherein the shape sensor is positioned at least partially within the second lumen.

24. The surgical system of claim 14, wherein the flexible needle comprises a plurality of concentric curved segments, wherein each of the plurality of concentric curved segments is independently rotatable and extendible.

25. The surgical system of claim 14, wherein the flexible needle comprises at least one control cable coupled to the actuator, and wherein flexion of the flexible needle is controlled by the control cable.

26. The surgical system of claim 14, wherein a distal tip of the flexible needle comprises a bevel tip.

27. The surgical system of claim 14, wherein the flexible needle comprises a solid needle tip.

28. The surgical system of claim 14, further comprising a second shape sensor attached to the flexible elongate needle body, at least a portion of the second shape sensor being substantially parallel to at least a portion of the shape sensor, wherein the connector is further adapted for connecting the second shape sensor to the processor for determining the shape of the flexible needle based on data from the shape sensor and the second shape sensor.

29. The surgical system of claim 28 wherein the each of the shape sensor and the second shape sensor are attached to different concentric curved segments of the flexible needle.

30. The surgical system of claim 14, further comprising a position sensor attached to a section of the flexible elongate needle body, the processor determining a position of the section based on data from the position sensor.

31. The surgical system of claim 30, wherein the position sensor is attached to a distal tip of the elongate needle body.

32. The surgical system of claim 31, further comprising a manual controller allowing direct user control over the actuator.

33. The surgical system of claim 14, further comprising a robotic surgical platform coupled to the actuator.

34. The surgical system of claim 14 wherein the flexible needle is a transcutaneous biopsy needle.

35. The surgical system of claim 14, wherein the flexible needle is an endoscopic biopsy needle.

36. The surgical system of claim 14, wherein the flexible needle is adapted to deliver a tissue ablation device.

37. The surgical system of claim 14, wherein the flexible needle is adapted to deliver radioactive seeds.

* * * * *